United States Patent [19]

Perkins

[11] Patent Number: 5,581,005

[45] Date of Patent: Dec. 3, 1996

[54] METHOD FOR MANUFACTURING COBALT CATALYSTS

[75] Inventor: Christopher M. Perkins, Cincinnati, Ohio

[73] Assignee: The Procter & Gamble Company, Cincinnati, Ohio

[21] Appl. No.: 490,699

[22] Filed: Jun. 16, 1995

[51] Int. Cl.$^6$ .................................................. C07F 15/06
[52] U.S. Cl. .................................................. 556/148
[58] Field of Search ............................................. 556/148

[56] References Cited

U.S. PATENT DOCUMENTS

| | | | |
|---|---|---|---|
| 4,218,377 | 8/1980 | Stockinger et al. | 260/326.22 |
| 4,325,884 | 4/1982 | Kang | 260/439 |
| 4,364,871 | 12/1982 | Svatek et al. | 260/439 |
| 4,425,278 | 1/1984 | Wirth et al. | 260/429 |
| 4,430,243 | 2/1984 | Bragg | 252/91 |
| 4,810,410 | 3/1989 | Diakun et al. | 252/102 |
| 4,915,854 | 4/1990 | Mao et al. | 252/8.8 |
| 5,089,162 | 2/1992 | Rapisarda et al. | 252/102 |
| 5,114,611 | 5/1992 | Van Kralingen et al. | 252/186.33 |
| 5,173,207 | 12/1992 | Drapier et al. | 252/99 |
| 5,244,594 | 9/1993 | Favre et al. | 252/186.33 |
| 5,246,612 | 9/1993 | Van Dijk et al. | 252/102 |

FOREIGN PATENT DOCUMENTS

| | | |
|---|---|---|
| 408131 | 1/1991 | European Pat. Off. . |
| 549271 | 6/1993 | European Pat. Off. . |
| 2054019 | 10/1971 | Germany . |

OTHER PUBLICATIONS

Application Ser. No. 08/382,742, Scheper et al., filed Feb. 2, 1995.
Application Ser. No. 08/382,546, Goldstein et al., Filed Feb. 2, 1995.
Application Ser. No. 382,750, Getty et al., Filed Feb. 2, 1995.
Application Ser. No. 08/508/198, Perkins et al., Filed Jul. 27, 1995.
Application Ser. No. 08/508,193, Scheper et al., Filed Jul. 27, 1995.
Application Ser. No. 08/508,197, Perkins et al., Filed Jul. 27, 1995.
Application Ser. No. 08/508,196, Haeggberg et al., Filed Jul. 27, 1995.
Application Ser. No. 08/508,195, Sivik, Filed Jul. 27, 1995.
Jackman et al., Inorg. Chem., vol. 18, No. 6, pp. 1497–1502 (1979).
M. L. Tobe, "Base Hydrolysis of Transition–Metal Complexes", Adv. Inorg. Bioinorg. Mech. (1983), 2, pp. 1–94.
G. M. Williams et al., "Coordination Complexes of Cobalt", J. Chem. Ed. (1989), 66(12), 1043–45.
W. L. Jolly, "The Synthesis and Characterization of Inorganic Compounds", (Prentice–Hall; 1970), pp. 461–463.
L. M. Jackman et al., "Synthesis of Transition–Metal Carboxylato Complexes", Inorg. Chem., 18, pp. 1497–1502 (1979).
T. J. Wierenga et al., "Synthesis and Characterization of Cobalt(III) Nicotinic Acid Complexes", Inorg. Chem., 21 (1982) pp. 2881–2885.
L. M. Jackman et al., "Reaction of Aquapentaamminecobalt(III) Perchlorate with Dicyclohexylcarbodiimide and Acetic Acid", Inorg. Chem., 18 (1979), pp. 2023–2025.
G. Schlessinger, "Carbonatotetramminecobalt(III) Nitrate", Inorg. Synthesis (1960) pp. 173–176.
F. Basolo et al., "Mechanism of Substitution Reactions in Complex Ions", Journal of Physical Chemistry, 56 (1952), pp. 22–25.
F. Basolo et al., "Acidopentamminecobalt(III) Salts", Inorg. Synthesis (1953), pp. 171–177.
Chan et al., "Octahedral Cobalt(m) Complexes and Reactions of the Chloropentakismethylaminecobalt(m) Cation", Anal. J. Chem., 1967, pp. 2229–2231.

Primary Examiner—Porfirio Nazario-Gonzalez
Attorney, Agent, or Firm—K. W. Zerby; J. J. Yetter; J. C. Rasser

[57] ABSTRACT

A method for manufacturing cobalt complexes having the formula:

$$[Co(NH_3)_5 M]T_y$$

wherein M ligands are selected from substituted and unsubstituted $C_1$–$C_{30}$ carboxylic acids having the formulas:

$$RC(O)O-;$$

said method comprising reacting cobalt complexes having the formula $[Co(NH_3)_5 X]T_y$ (e.g., X is chlorine) with concentrated ammonium hydroxide followed by carboxylic acid anhydride of the formula $RC(O)O(O)CR$.

13 Claims, No Drawings

METHOD FOR MANUFACTURING COBALT CATALYSTS

TECHNICAL FIELD

The present invention relates to methods for manufacturing cobalt complexes having the formula:

$$[Co(NH_3)_5M]T_y$$

wherein M ligand is selected from substituted and unsubstituted $C_1$–$C_{30}$ carboxylic acids having the formula:

$$RC(O)O\text{—}.$$

These catalysts are particularly useful in bleach-containing consumer compositions, especially automatic dishwashing detergents and laundry detergents comprising bleach.

BACKGROUND OF THE INVENTION

Cobalt catalysts are well known, as are a variety of methods for manufacturing them. Most synthesis methods, however, are directed simply to methods effective for obtaining experimental quantities for academic studies. These are described, for example, in M. L. Tobe, "Base Hydrolysis of Transition-Metal Complexes", *Adv. Inorg. Bioinorg. Mech.*, (1983), 2, pages 1–94; *J. Chem. Ed.* (1989), 66 (12), 1043–45; The Synthesis and Characterization of Inorganic Compounds, W. L. Jolly (Prentice-Hall; 1970), pp. 461–3; *Inorg. Chem.*, 18, 1497–1502 (1979); *Inorg. Chem.*, 21, 2881–2885 (1982); *Inorg. Chem.*, 18, 2023–2025 (1979); *Inorg. Synthesis*, 173–176 (1960); and *Journal of Physical Chemistry*, 56, 22–25 (1952).

For use in consumer products, however, it is necessary that the cobalt catalysts be prepared in large quantities by the most cost effective manner with the highest possible purity. It has been discovered by the present invention that cobalt catalysts containing carboxylate ligands can be prepared on an industrially useful scale by the present process.

BACKGROUND ART

U.S. Pat. No. 4,810,410, to Diakun et al, issued Mar. 7, 1989; U.S. Pat. No. 5,246,612, to Van Dijk et al., issued Sep. 21, 1993; U.S. Pat. No. 5,244,594, to Favre et al., issued Sep. 14, 1993; and European Patent Application, Publication No. 408,131, published Jan. 16, 1991 by Unilever NV, see also: U.S. Pat. No. 5,114,611, to Van Kralingen et al, issued May 19, 1992 (transition metal complex of a transition metal, such as cobalt, and a non-macro-cyclic ligand); U.S. Pat. No. 4,430,243, to Bragg, issued Feb. 7, 1984 (laundry bleaching compositions comprising catalytic heavy metal cations, including cobalt); German Patent Specification 2,054,019, published Oct. 7, 1971 by Unilever N.V. (cobalt chelant catalyst); and European Patent Application Publication No. 549,271, published Jun. 30, 1993 by Unilever PLC (macrocyclic organic ligands in cleaning compositions).

SUMMARY OF THE INVENTION

The present invention relates to methods for manufacturing cobalt complexes having the formula:

$$[Co(NH_3)_5M]T_y$$

wherein the M ligand is selected from substituted and unsubstituted $C_1$–$C_{30}$ carboxylic acids having the formula:

$$RC(O)O\text{—};$$

said method comprising the steps of:

(a) reacting a cobalt (III) pentaamine complex having the formula:

$$[Co(NH_3)_5X]T_y$$

wherein X is selected from base labile ligands (preferably $Cl^-$, $Br^-$, $OH^-$, $H_2O$, $NO_2^-$, $SO_4^{2-}$, and $CO_3^{2-}$); and T is one or more counteranions present in a number y, where y is an integer to obtain a charge-balanced salt (preferably y is 1 or 2);

with an aqueous base (preferably concentrated ammonium hydroxide); followed by (b) reacting the product of step (a) with a carboxylic acid anhydride of the formula:

$$RC(O)O(O)CR$$

wherein each R is independently selected from substituted or unsubstituted $C_1$–$C_{30}$ moieties (preferably both R are the same); and (c) collecting the cobalt complex.

All parts, percentages and ratios used herein are expressed as percent weight unless otherwise specified. All documents cited are, in relevant part, incorporated herein by reference.

DETAILED DESCRIPTION OF THE INVENTION

The present invention relates to a method for manufacturing cobalt complexes having the formula:

$$[Co(NH_3)_5M]T_y$$

wherein the M ligands are selected from substituted and unsubstituted $C_1$–$C_{30}$ carboxylic acids having the formulas:

$$RC(O)O\text{—}.$$

This method comprises the first step of reacting with an aqueous base a cobalt (III) pentaamine complex having the formula:

$$[Co(NH_3)_5X]T_y$$

wherein X is selected from base labile ligands. Preferred X are selected from $Cl^-$, $Br^-$, $OH^-$, $H_2O$, $NO_2^-$, $SO_4^{2-}$, and $CO_3^{2-}$. T is one or more appropriately selected counteranions present in a number y, where y is an integer to obtain a charge-balanced salt (preferably y is 1 or 2). Preferred T are selected from the group consisting of chloride, nitrate, nitrite, sulfate, citrate, acetate, carbonate, bromide, $PF_6^-$, $BF_4^-$, phosphate, tosylate, methanesulfonate, and combinations thereof.

The aqueous base for this first step is preferably concentrated aqueous ammonium hydroxide (preferably at least 20%, more preferably at least 25%, and typically between 28–32% solutions). Other aqueous bases include, for example, potassium hydroxide, sodium hydroxide, and other weak amine bases.

Reaction conditions for this step typically require slight heating (above about 65° C.) sufficient to dissolve the cobalt (III) pentaamine complex, followed by cooling to approximately room temperature prior to the next step.

This first step is followed by reacting the product of the first step with a carboxylic acid anhydride of the formula:

RC(O)O(O)CR wherein each R is independently selected from substituted or unsubstituted $C_1$–$C_{30}$ moieties. It is preferred that both R moieties are the same, but mixed anhydrides may be used as desired for the desired cobalt complex being synthesized. Reaction conditions for this step are typically room temperature for from about 10 to about 60 minutes.

At the end of the reaction process, the cobalt complex is collected. Preferred collection methods include, for example, evaporation to remove the solvent or lyophilization. The cobalt complex collected may be used as is, or further purified or modified for incorporation into the desired product or use to be made of the complex. This includes optionally washing the solid product with ethanol to remove non-cobalt salts.

The present invention method preferably is carried out in one reaction vessel without isolation or separation of the intermediate reaction products. However, if desired, one or more of the reaction steps may be conducted in separate reaction vessels, and may be followed or preceeded by optional separation and/or collection steps of the intermediate reaction materials.

Herein, R is preferably selected from the group consisting of hydrogen and $C_1$–$C_{30}$ (preferably $C_1$–$C_{18}$) unsubstituted and substituted alkyl, $C_6$–$C_{30}$ (preferably $C_6$–$C_{18}$) unsubstituted and substituted aryl, and $C_3$–$C_{30}$ (preferably $C_5$–$C_{18}$) unsubstituted and substituted heteroaryl, wherein substituents are selected from the group consisting of $-NR'_3$, $-NR'^+_4$, $-C(O)OR'$, $-OR'$, $-C(O)NR'_2$, wherein R' is selected from the group consisting of hydrogen and $C_1$–$C_6$ moieties. Such substituted R therefore include the moieties $-(CH_2)_nOH$ and $-(CH_2)_nNR'^+_4$, wherein n is an integer from 1 to about 16, preferably from about 2 to about 10, and most preferably from about 2 to about 5.

Most preferred M are carboxylic acids having the formula above wherein R is selected from the group consisting of hydrogen, methyl, ethyl, propyl, straight or branched $C_4$–$C_{12}$ alkyl, and benzyl. Most preferred R is methyl. Preferred carboxylic acid M moieties include formic, benzoic, octanoic, nonanoic, decanoic, dodecanoic, and especially acetic acid. Therefore, most preferred methods use the anhydrides comprising these carboxylic acids, and preferred anhydrides are the same acids. Most preferred anhydride is acetic anhydride.

The most preferred cobalt complex prepared by the present invention is cobalt pentaamine acetate chloride, $[Co(NH_3)_5OAc]Cl_2$ (herein "PAC").

The starting cobalt (III) pentaamine complexes useful herein, the $[Co(NH_3)_5X]T_y$ complexes, are commercially available and can be prepared by a variety of methods. These include the preferred starting material $[Co(NH_3)_5Cl]Cl_2$, sold by Aldrich and by Pfaltz and Bauer.

The following nonlimiting example further illustrates the method according to the present invention.

Synthesis of $[Co(NH_3)_5OAc]Cl_2$

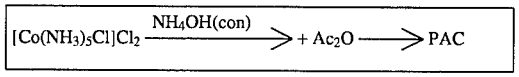

$[Co(NH_3)_5Cl]Cl_2$ (26.4 g, 0.10 mol) is added to distilled water (800 mL). $NH_4OH$ (23.4 mL, 0.600 mol) is slowly added with stirring. The solution is then heated to 75° C. and the solid dissolves with stirring. The solution is cooled to RT. Acetic anhydride (30.6 g, 0.30 mol) is slowly added with stirring. The solution is stirred 1 hour at RT. At this point the reaction solution can either be lyophilized to a pink powder or the solution can be rotovapped down and the resulting solid pumped on overnight at 0.05 mm. to remove residual water and $NH_4OAc$. The excess ammonium acetate and ammonium chloride salts can also be removed by washing the solid with ethanol. Yield 35 gr., 78.1% by uv-vis spectroscopy. HPLC [according to the method of D. A. Buckingham, et al, *Inorg. Chem.*, 28, 4567–4574 (1989)] shows all of the cobalt is present as $[Co(NH_3)_5OAc]Cl_2$.

What is claimed is:

1. A method for manufacturing cobalt complexes having the formula:

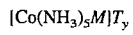

wherein the M ligand is selected from substituted and unsubstituted $C_1$–$C_{30}$ carboxylic acids having the formula:

wherein R is selected from substituted or unsubstituted $C_1$–$C_{30}$ moieties; said method comprising the steps of:
(a) reacting a cobalt (III) pentaamine complex having the formula:

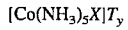

wherein X is selected from base labile ligands; and T is one or more counteranions present in a number y, where y is an integer to obtain a charge-balanced salt;

with ammonium hydroxide; followed by
(b) reacting the product of step (a) with a carboxylic acid anhydride of the formula:

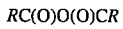

wherein each R is independently selected from substituted or unsubstituted $C_1$–$C_{30}$ moieties; and
(c) collecting the cobalt complex.

2. The method according to claim 1 wherein X is selected from $Cl^-$, $Br^-$, $OH^-$, $H_2O$, $NO_2^-$, $SO_4^{2-}$, and $CO_3^{2-}$.

3. The method according to claim 1 wherein each R in the anhydride is independently selected from the group consisting of hydrogen and $C_1$–$C_{30}$ unsubstituted and substituted alkyl, $C_6$–$C_{30}$ unsubstituted and substituted aryl, and $C_3$–$C_{30}$ unsubstituted and substituted heteroaryl, wherein substituents are selected from the group consisting of $-NR'_3$, $-NR'^+_4$, $-C(O)OR'$, $-OR'$, $-C(O)NR'_2$, wherein R' is selected from the group consisting of hydrogen and $C_1$–$C_6$ moieties.

4. The method according to claim 3 wherein each R in the anhydride is independently selected from $C_1$–$C_{18}$ unsubstituted and substituted alkyl.

5. The method according to claim 4 wherein each R in the anhydride is independently selected from the group consisting of hydrogen, methyl, ethyl, propyl, straight or branched $C_4$–$C_{12}$ alkyl, and benzyl.

6. The method according to claim 5 wherein R is methyl.

7. The method according to claim 4 wherein each R is independently selected from the moieties $-(CH_2)_nOH$ and $-(CH_2)_nNR'^+_4$, wherein n is an integer from 1 to about 16.

8. The method according to claim 1 wherein the M ligand is a carboxylic acid moiety selected from formic, benzoic, octanoic, nonanoic, decanoic, dodecanoic, and acetic acid.

9. The method according to claim 8 wherein M is an acetic acid moiety.

10. A method for manufacturing cobalt complexes having the formula:

[Co(NH$_3$)$_5$M]T$_y$ wherein the M ligand is selected from substituted and unsubstituted C$_1$–C$_{30}$ carboxylic acids having the formula:

RC(O)O—;

wherein R is selected from C$_1$–C$_{18}$ unsubstituted and substituted alkyl moieties; said method comprising the steps of:
(a) reacting a cobalt (III) pentaamine complex having the formula:

[Co(NH$_3$)$_5$X]T$_y$ wherein X is selected from Cl$^-$, Br$^-$, OH$^-$, H$_2$O, NO$_2^-$, SO$_4^{2-}$, and CO$_3^{2-}$, and T is one or more counteranions present in a number y, where y is an integer to obtain a charge-balanced salt; with concentrated ammonium hydroxide; followed by
(b) reacting the product of step (a) with a carboxylic acid anhydride of the formula:

RC(O)O(O)CR wherein each R is independently selected from C$_1$–C$_{18}$ unsubstituted and substituted alkyl moieties; and
(c) collecting the cobalt complex.

11. The method according to claim 10 wherein both R in the anhydride are the same moiety selected from the group consisting of hydrogen, methyl, ethyl, propyl, straight or branched C$_4$–C$_{12}$ alkyl, and benzyl.

12. The method according to claim 11 wherein the anhydride is acetic anhydride.

13. The method according to claim 10 wherein each R in the anhydride is independently selected from the moieties —(CH$_2$)$_n$OH and —(CH$_2$)$_n$NR'$_4^+$, wherein n is an integer from about 2 to about 10.

* * * * *